(12) United States Patent
Paris

(10) Patent No.: US 7,668,590 B1
(45) Date of Patent: Feb. 23, 2010

(54) METHODS AND DEVICES FOR DETERMINING EXERCISE DIAGNOSTIC PARAMETERS

(75) Inventor: Michael Paris, San Francisco, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 754 days.

(21) Appl. No.: 11/351,401

(22) Filed: Feb. 10, 2006

Related U.S. Application Data

(62) Division of application No. 10/828,883, filed on Apr. 20, 2004, now Pat. No. 7,031,766.

(51) Int. Cl.
*A61B 5/04* (2006.01)

(52) U.S. Cl. ............ 600/519; 600/509; 607/17; 607/18; 607/19

(58) Field of Classification Search .......... 600/500, 600/509, 513, 519; 607/6, 17–19
See application file for complete search history.

(56) References Cited

U.S. PATENT DOCUMENTS

| | | | |
|---|---|---|---|
| 4,390,021 A | 6/1983 | Spurrell et al. | |
| 4,393,877 A | 7/1983 | Imran et al. | |
| 4,686,988 A | 8/1987 | Sholder | 128/419 PT |
| 4,708,142 A | 11/1987 | DeCote, Jr. | 128/419 PT |
| 4,712,555 A | 12/1987 | Thornander et al. | 128/419 PT |
| 4,729,376 A | 3/1988 | DeCote, Jr. | 128/419 PT |
| 4,788,980 A | 12/1988 | Mann et al. | 128/419 PG |
| 4,809,697 A | 3/1989 | Causey, III et al. | 128/419 PT |
| 4,872,459 A | 10/1989 | Pless | 607/15 |
| 4,938,228 A | 7/1990 | Righter | |
| 4,940,952 A | 7/1990 | Kegasa | 331/11 |
| 4,944,298 A | 7/1990 | Sholder | 128/419 PG |
| 4,944,299 A | 7/1990 | Silvian | 128/419 PG |
| 4,969,465 A | 11/1990 | Pless et al. | |
| 4,969,467 A | 11/1990 | Callaghan et al. | 128/419 PG |
| 4,971,058 A | 11/1990 | Pless et al. | |
| 5,065,759 A | 11/1991 | Begemann et al. | |
| 5,133,350 A | 7/1992 | Duffin | |
| 5,144,949 A | 9/1992 | Olson | |

(Continued)

FOREIGN PATENT DOCUMENTS

WO    WO 00/64336 A1    11/2000

(Continued)

OTHER PUBLICATIONS

Non-Final Office Action mailed Feb. 23, 2009: Related U.S. Appl. No. 11/561,267.

(Continued)

*Primary Examiner*—Carl H Layno
*Assistant Examiner*—Luther G Behringer
(74) *Attorney, Agent, or Firm*—Steven M. Mitchell; Theresa A. Takeuchi

(57) ABSTRACT

A device, such as an implantable cardiac device, and methods for determining exercise diagnostic parameters of a patient are disclosed. Specifically, a maximum observed heart rate of a patient during exercise can be identified when an activity level and a heart rate measurement of the patient exceed predetermined thresholds. Included are methods for filtering out premature heartbeats or noise from the maximum heart rate determination. Methods of determining other exercise parameters, such as workload are also disclosed. The device includes hardware and/or software for performing the described methods.

14 Claims, 11 Drawing Sheets

U.S. PATENT DOCUMENTS

| | | | |
|---|---|---|---|
| 5,284,491 | A | 2/1994 | Sutton et al. |
| 5,292,340 | A | 3/1994 | Crosby |
| 5,327,900 | A | 7/1994 | Mason et al. |
| 5,350,410 | A | 9/1994 | Kleks et al. .................. 607/28 |
| 5,549,649 | A | 8/1996 | Florio |
| 5,720,769 | A | 2/1998 | van Oort et al. |
| 5,738,104 | A | 4/1998 | Lo |
| 6,045,513 | A | 4/2000 | Stone et al. ................. 600/508 |
| 6,081,747 | A | 6/2000 | Levine |
| 6,102,874 | A | 8/2000 | Stone et al. ................. 600/595 |
| 6,190,324 | B1 | 2/2001 | Kieval et al. ................ 600/483 |
| 6,275,734 | B1 | 8/2001 | McClure et al. .............. 607/27 |
| 6,280,409 | B1 | 8/2001 | Stone et al. .................. 604/67 |
| 6,285,907 | B1 | 9/2001 | Kramer |
| 6,361,503 | B1 | 3/2002 | Starobin et al. ............. 600/508 |
| 6,411,848 | B2 | 6/2002 | Kramer |
| 6,438,408 | B1 | 8/2002 | Mulligan et al. ............ 600/510 |
| 6,477,420 | B1 | 11/2002 | Struble |
| 6,501,988 | B2 | 12/2002 | Kramer |
| 6,529,771 | B1 | 3/2003 | Kieval et al. ................ 600/509 |
| 6,648,829 | B2 | 11/2003 | Starobin et al. ............. 600/508 |
| 6,648,830 | B2 | 11/2003 | Starobin et al. ............. 600/508 |
| 6,904,313 | B1 | 6/2005 | Snell |
| 7,031,766 | B1 | 4/2006 | Paris |
| 7,043,294 | B1 | 5/2006 | Paris |
| 7,142,918 | B2 | 11/2006 | Stahmann |
| 7,149,568 | B2 * | 12/2006 | Amano et al. ............... 600/513 |
| 7,192,401 | B2 * | 3/2007 | Saalasti et al. .............. 600/500 |
| 7,330,752 | B2 * | 2/2008 | Kettunen et al. ............ 600/513 |
| 2001/0016759 | A1 | 8/2001 | Kramer |
| 2002/0082648 | A1 | 6/2002 | Kramer |
| 2002/0082660 | A1 | 6/2002 | Stahmann |
| 2002/0115939 | A1 | 8/2002 | Mulligan et al. ............ 600/510 |
| 2002/0151806 | A1 | 10/2002 | Starobin et al. ............. 600/509 |
| 2002/0151811 | A1 | 10/2002 | Starobin et al. ............. 600/520 |
| 2003/0069610 | A1 | 4/2003 | Kramer |
| 2003/0074029 | A1 | 4/2003 | Deno et al. ................... 607/23 |
| 2003/0149370 | A1 | 8/2003 | Starobin et al. ............. 600/515 |
| 2003/0187479 | A1 | 10/2003 | Thong |
| 2003/0208106 | A1 | 11/2003 | Anderson et al. ........... 600/300 |
| 2005/0065443 | A1 | 3/2005 | Ternes ........................ 600/509 |
| 2005/0187585 | A1 | 8/2005 | Mussig |

FOREIGN PATENT DOCUMENTS

| | | |
|---|---|---|
| WO | WO 0071202 A1 | 11/2000 |
| WO | WO 02/053026 A2 | 7/2002 |
| WO | WO 02/053026 A3 | 7/2002 |
| WO | WO 02/053228 A1 | 7/2002 |
| WO | WO 02051496 A2 | 7/2002 |
| WO | WO 02051496 A3 | 7/2002 |
| WO | WO 03/057032 A1 | 7/2003 |
| WO | WO 03/057033 A1 | 7/2003 |

OTHER PUBLICATIONS

Non-Final Office Aciton mailed Sep. 29, 2005: Related U.S. Appl. No. 10/828,897.

Non-Final Office Action mailed Apr. 1, 2009; Related U.S. Appl. No. 11/405,129.

Non-Final Office Action mailed Oct. 13, 2005: Related U.S. Appl. No. 10/828,883.

Notice of Allowance mailed Jan. 20, 2006: Related U.S. Appl. No. 10/828,897.

Notice of Allowance mailed Jan. 10, 2006: Related U.S. Appl. No. 10/828,883.

Non-Final Office Action mailed Jul. 10, 2009: Related U.S. Appl. No. 11/351,859.

* cited by examiner

METHODS AND DEVICES FOR DETERMINING EXERCISE DIAGNOSTIC PARAMETERS

PRIORITY CLAIM

The present application is a divisional of, and claims priority to, U.S. patent application Ser. No. 10/828,883, now U.S. Pat. No. 7,031,766, entitled "METHODS AND DEVICES FOR DETERMINING EXERCISE DIAGNOSTIC PARAMETERS," filed Apr. 20, 2004.

CROSS REFERENCE TO RELATED APPLICATIONS

The present invention relates to the following commonly assigned application, which is incorporated herein by reference: U.S. patent application Ser. No. 11/351,859, entitled "Methods and Devices for Determining Exercise Diagnostic Parameters," filed Feb. 10, 2006.

BACKGROUND OF THE INVENTION

1. Field of the Invention

The present invention relates generally to implantable cardiac devices and, more particularly, to an implantable cardiac device with the capability of measuring exercise diagnostic parameters.

2. Background Art

An implantable cardiac device is a medical device that is implanted in a patient to monitor electrical activity of the heart and to deliver appropriate electrical and/or drug therapy, as required. Implantable cardiac devices include, for example, pacemakers, cardioverters and defibrillators. The term "implantable cardioverter defibrillator" or simply "ICD" is used herein to refer to any implantable cardiac device. An ICD employs a battery to power its internal circuitry and to generate electrical therapy. The electrical therapy can include, for example, pacing pulses, cardioverting pulses and/or defibrillator pulses.

Heart failure is a growing medical challenge. In clinical practice today, most patients are managed effectively through pharmacological therapy such as beta-blockers, ACE inhibitors, and diuretics. If a patient's condition worsens, treatment may become more aggressive to include biventricular pacing and other implantable cardiac device therapy. Along with providing the primary objectives in the treatment of heart failure of improving symptoms, increasing the quality of life, and slowing disease progression, devices need to provide heart failure physicians with diagnostic parameters to monitor the patient's progress.

Currently, medical history and physical examination are the most important tools that a physician uses to determine and mark the progress of a heart failure patient. This involves much of the physician's time with the patient, as this may lead to the primary management program for the patient.

Included in most management programs is an exercise routine. It has been written extensively that adherence to exercise is a priority in improving or in maintaining good heath. Exercise diagnostics may help clinicians assess the compliance of the management programs prescribed to their patients, and possibly assist the patient in meeting those goals.

During exercise, the heart rate is a parameter or indicator of the amount of work that was required to provide blood and oxygen to the body. The maximum heart rate for a level of exercise corresponds to the conditioning of the heart. Other parameters, such as heart rate intensity, percent oxygen consumption (% $VO_2$) reserve, metabolic equivalents (METS), and workload also provide data that is indicative of heart conditioning.

Heart rate recovery after exercise is evaluated as a clinical marker of good vagal activity and cardiac health. As the heart rate increases due to a reduction in vagal tone, the heart rate also decreases with a reactivation of vagal activity. A delayed response to the decreasing heart rate may be a good prognostic marker of overall mortality (Cole, C. et al., NEJM 341:18, 1351-1357 (1999)) and cardiac health. Cole suggests that a reduction of only 12 beats per minute after one minute from peak exercise has been shown to be an abnormal value.

It would be advantageous to be able to obtain accurate exercise diagnostics over time from the patient without the cost and time of a physical examination, such as, for example, a treadmill test.

BRIEF SUMMARY OF THE INVENTION

The inventor has discovered that a device, such as an implantable medical device, can be used to determine exercise diagnostics in a patient, minimizing time and expense in monitoring a patient's progress.

The present invention includes a device, such as an implantable cardiac device, and method for determining a maximum observed heart rate of a patient during exercise. The method includes monitoring a changing heart rate of the patient and producing heart rate measurements, monitoring activity level of the patient, and identifying a heart rate as the maximum observed heart rate. The maximum observed heart rate is identified when the activity level exceeds an activity threshold, a heart rate measurement is greater than a stored heart rate measurement, and a difference between the heart rate measurement and the stored heart rate measurement does not exceed a predetermined threshold.

The present invention also includes a device, such as an implantable cardiac device, and method for determining workload of a patient during exercise. The method includes monitoring a changing heart rate of the patient and producing heart rate measurements, monitoring activity level of the patient, and determining workload of the patient using at least one heart rate measurement when the activity level exceeds an activity threshold.

The present invention also includes a device, such as an implantable cardiac device, and method for determining heart rate recovery of a patient. The method includes monitoring a changing heart rate of the patient and producing heart rate measurements, identifying a first heart rate, identifying a second heart rate, and using the first heart rate and the second heart rate to determine a measure of heart rate recovery. The first heart rate is identified when at least one heart rate measurement exceeds a first heart rate measurement threshold and/or an activity level of the patient exceeds a first activity threshold. The second heart rate is identified when at least one heart rate measurement falls below a second heart rate measurement and/or an activity level of the patient falls below a second activity threshold.

The embodiments of the present invention related to the device for determining a maximum observed heart rate of a patient during exercise, determining workload of a patient during exercise, and determining heart recovery of a patient include means for performing the above-described methods.

Further features and advantages of the present invention as well as the structure and operation of various embodiments of the present invention are described in detail below with reference to the accompanying drawings.

BRIEF DESCRIPTION OF THE DRAWINGS/FIGURES

The accompanying drawings, which are incorporated herein and form part of the specification, illustrate the present invention and, together with the description, further serve to explain the principles of the invention and to enable a person skilled in the relevant art(s) to make and use the invention. In the drawings, like reference numbers indicate identical or functionally similar elements. Additionally, in most drawings, the leftmost digit of a reference number identifies the drawing in which the reference number first appears.

FIG. 3A, FIG. 3B, FIG. 3C, and FIG. 3D illustrate representations of sample exercise diagnostic results in accordance with the present invention.

Figure 4:
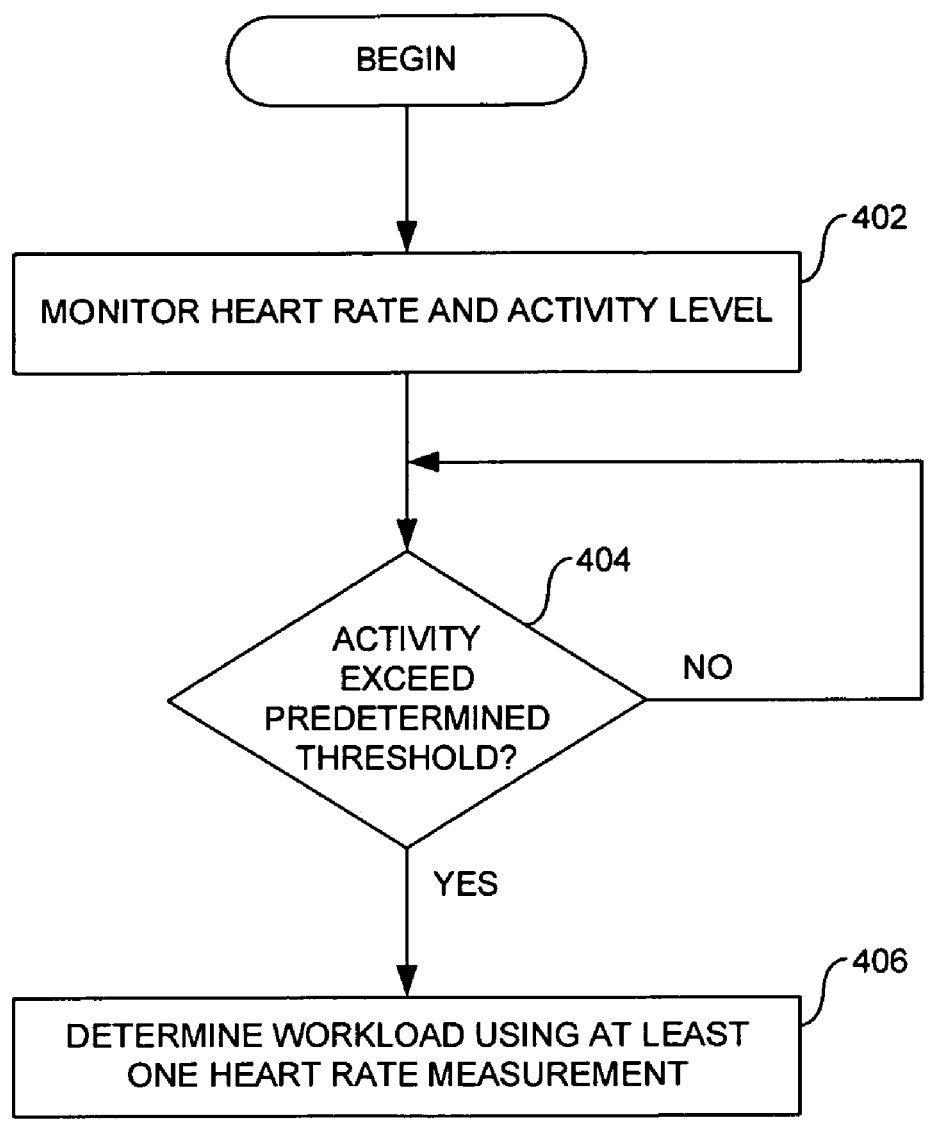

FIG. 4 is a flow chart illustrating an embodiment of a method for determining an exercise diagnostic such as work of a patient during exercise in accordance with the present invention.

Figure 5:
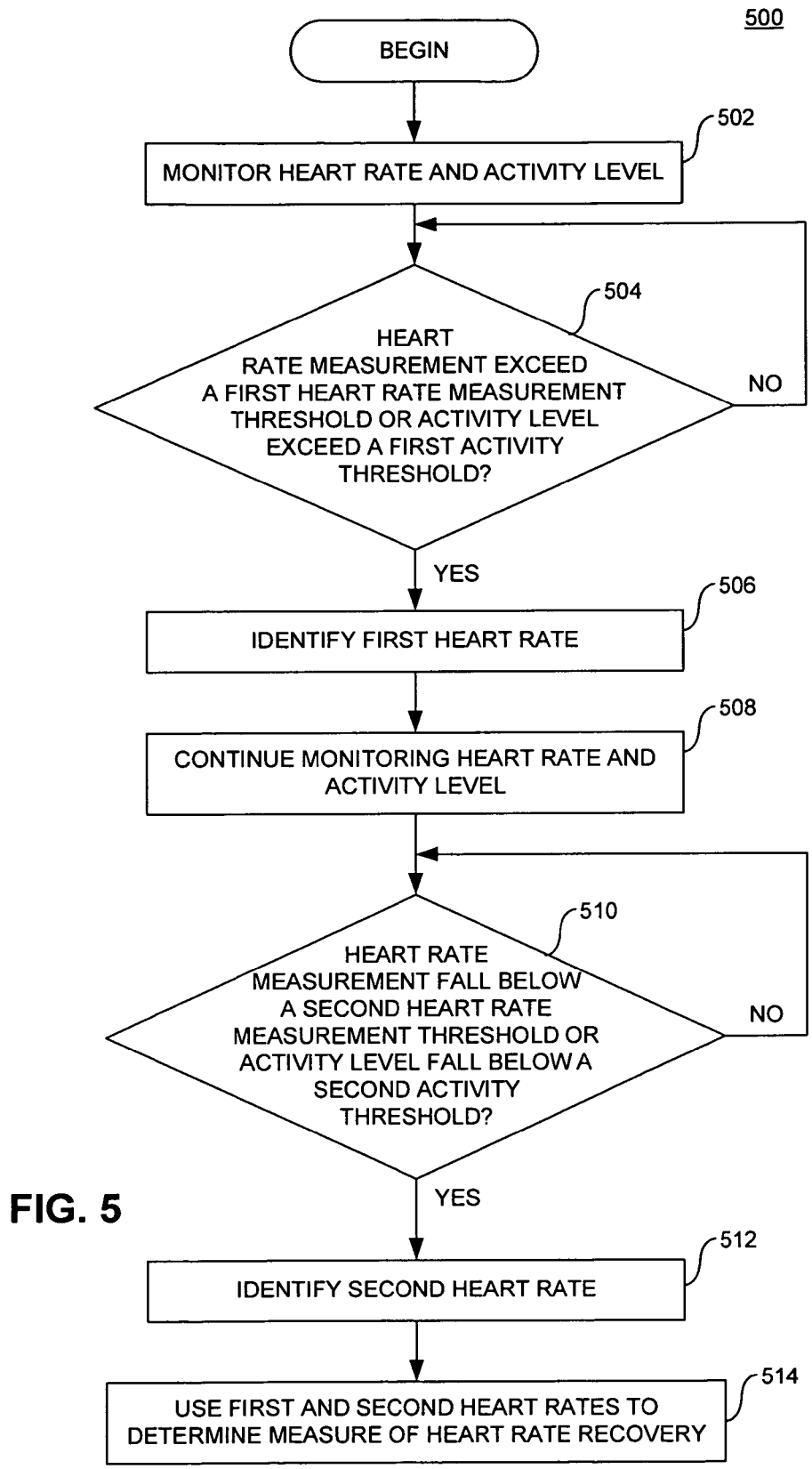

FIG. 5 is a flow chart illustrating an embodiment of a method for determining heart rate recovery of a patient after exercise in accordance with the present invention.

Figure 6:
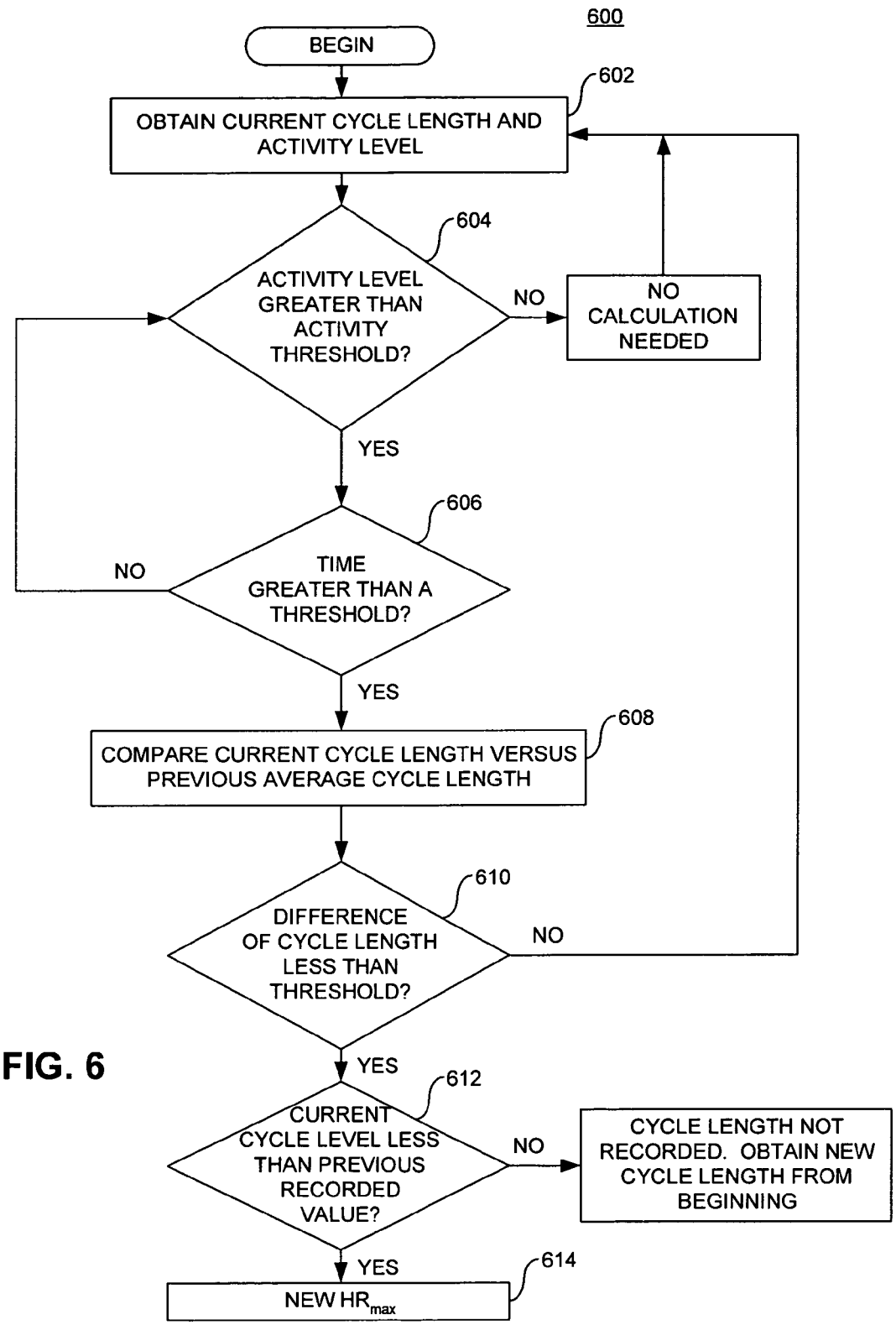

FIG. 6 is a flow chart illustrating another embodiment of a method for determining an observed maximum heart rate of a patient during exercise in accordance with the present invention, as described in a first example.

Figure 7:
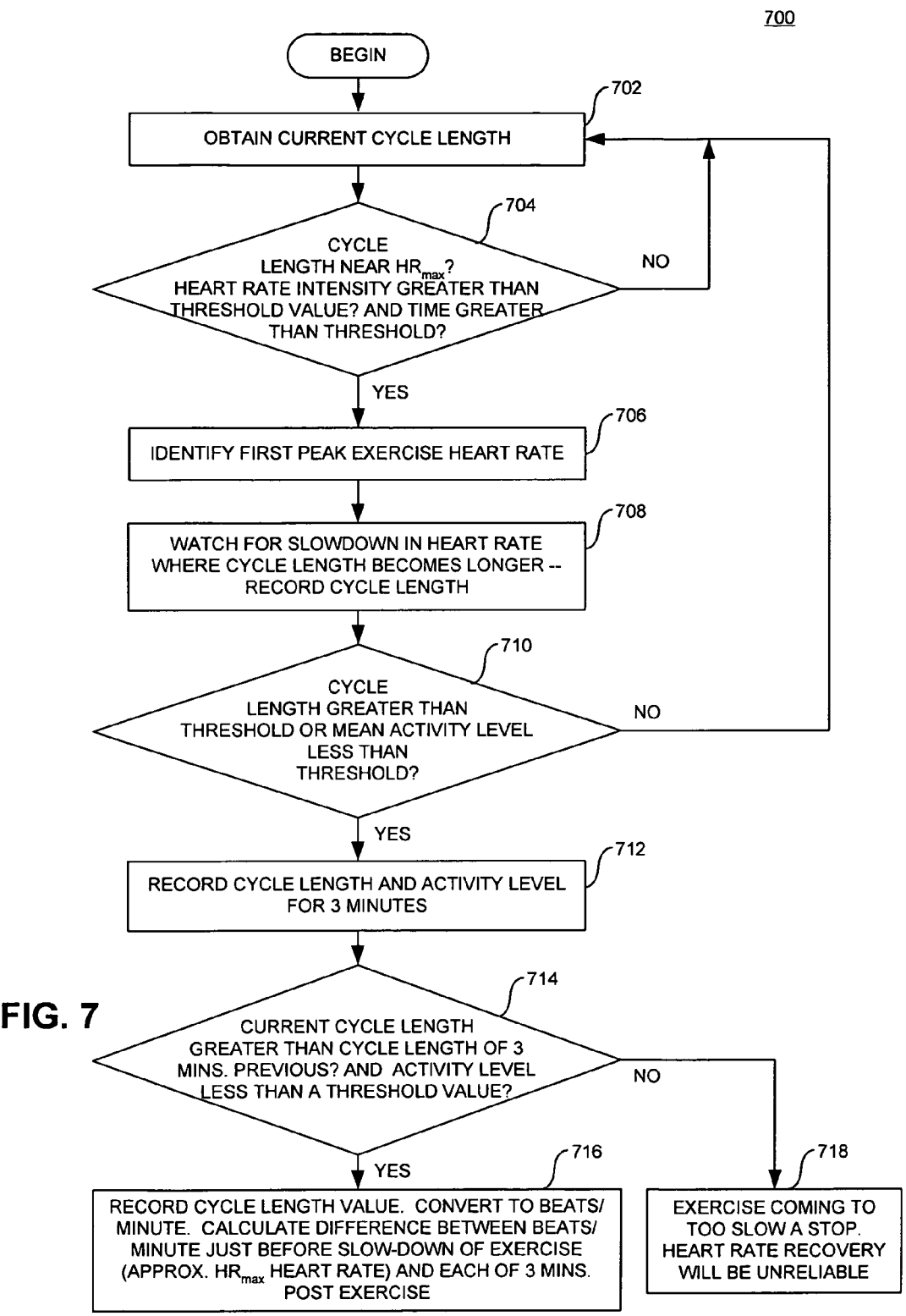

FIG. 7 is a flow chart illustrating another embodiment of a method for determining heart rate recovery of a patient in accordance with the present invention, as described in a second example.

DETAILED DESCRIPTION OF THE INVENTION

The following detailed description of the present invention refers to the accompanying drawings that illustrate exemplary embodiments consistent with this invention. Other embodiments are possible, and modifications may be made to the embodiments within the spirit and scope of the present invention. Therefore, the following detailed description is not meant to limit the invention. Rather, the scope of the invention is defined by the appended claims.

It will be apparent to one of skill in the art that the present invention, as described below, may be implemented in many different embodiments of hardware, software, firmware, and/or the entities illustrated in the figures. Any actual software and/or hardware described herein is not meant to limit the scope of the present invention. Thus, the structure, operation and behavior of the present invention will be described with the understanding that many modifications and variations of the embodiments are possible, given the level of detail presented herein.

Figure 1A:
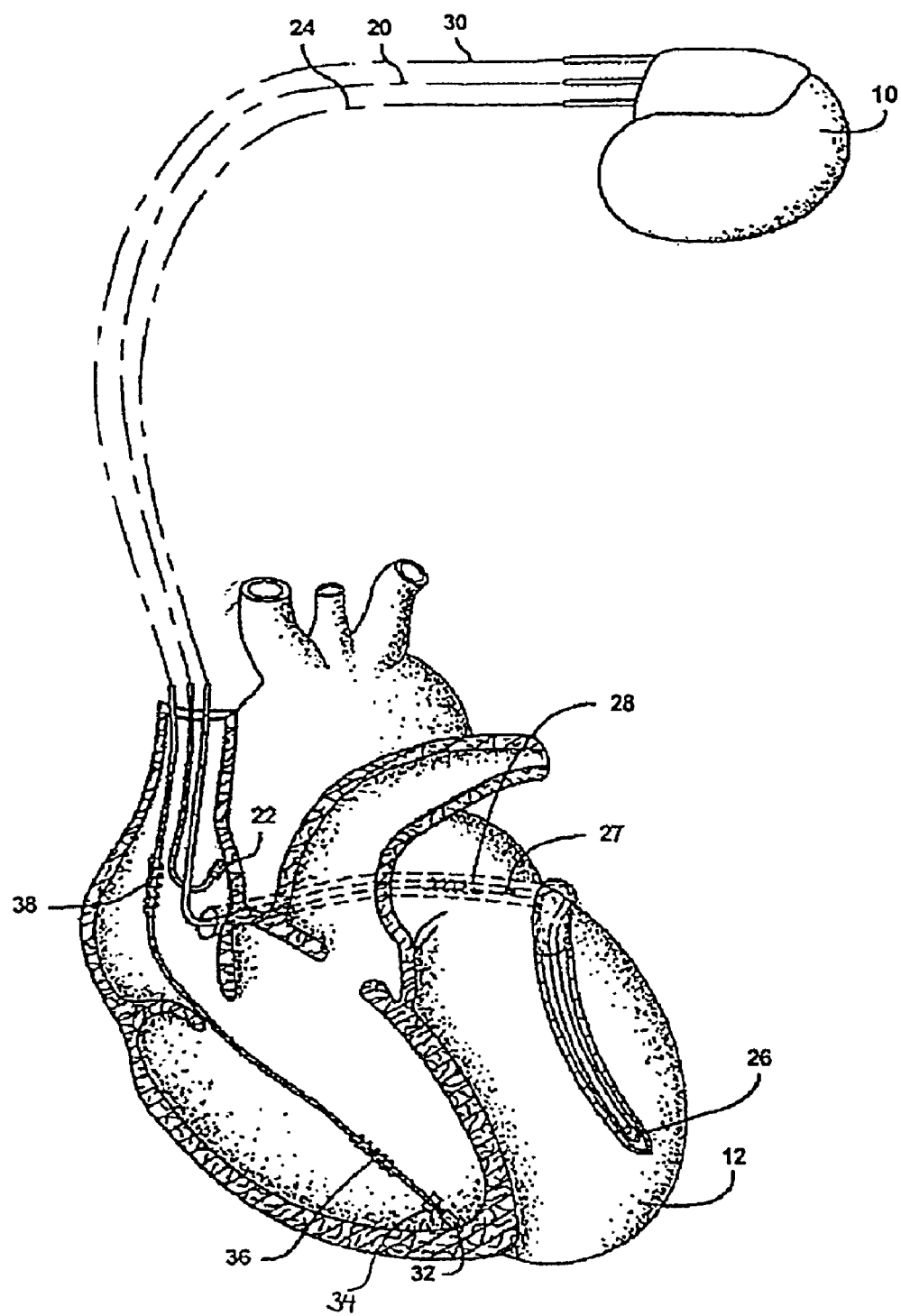
FIG. 1A is a simplified diagram illustrating an exemplary ICD in electrical communication with at least three leads implanted into a patient's heart for delivering multi-chamber stimulation and shock therapy.
Figure 1B:
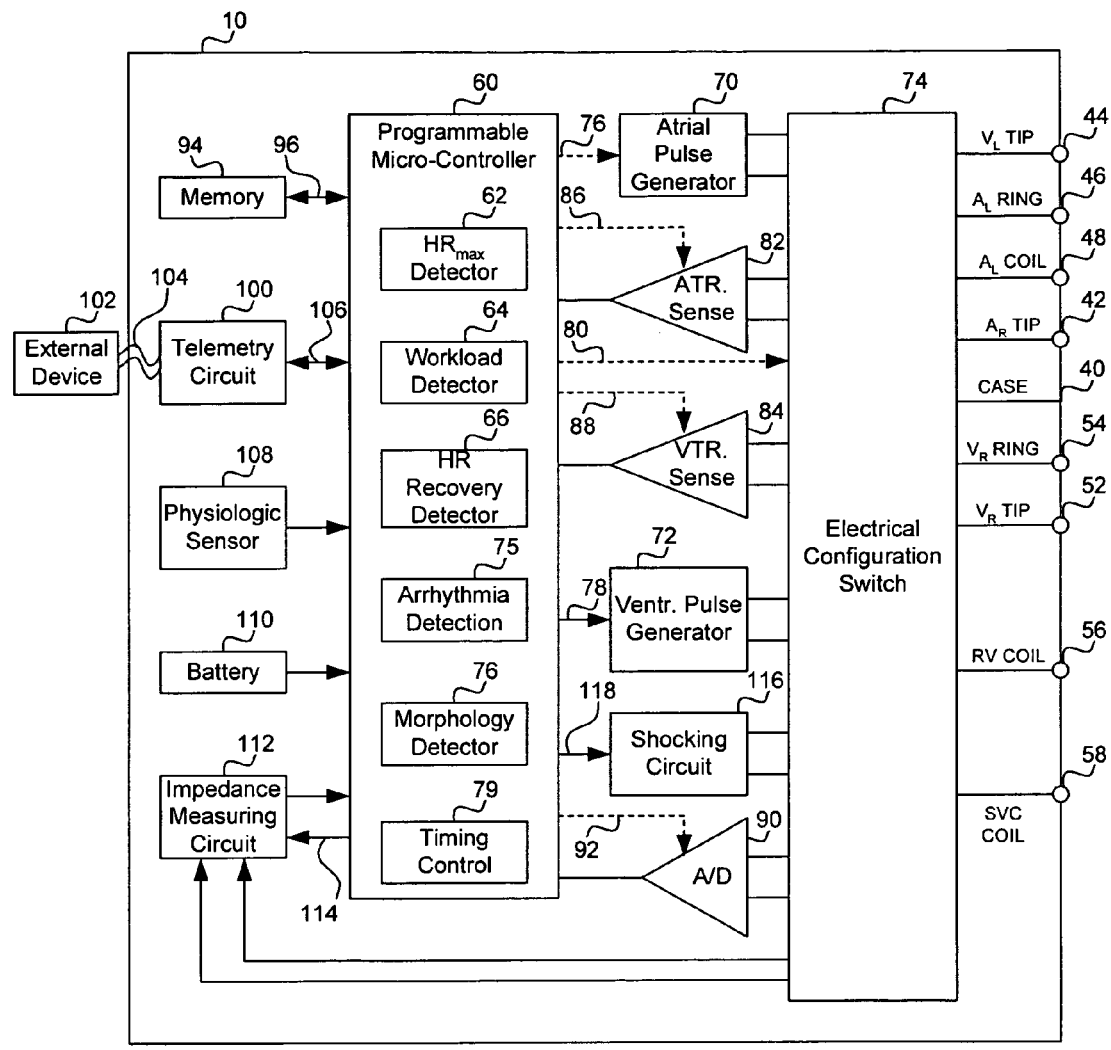
FIG. 1B is a functional block diagram of an exemplary ICD, which can provide cardioversion, defibrillation and pacing stimulation in four chambers of a heart.

Before describing the invention in detail, it is helpful to describe an example environment in which the invention may be implemented. The present invention is particularly useful in the environment of an implantable cardiac device. Implantable cardiac devices include, for example, pacemakers, cardioverter-defibrillators, and hemodynamic monitors. The term "implantable cardioverter defibrillator" or simply "ICD" is used herein to refer to any implantable cardiac device or implantable cardioverter-defibrillator. FIGS. 1A and 1B illustrate such an environment.

As shown in FIG. 1A, there is an exemplary ICD 10 in electrical communication with a patient's heart 12 by way of three leads, 20, 24 and 30, suitable for delivering multi-chamber stimulation and pacing therapy. To sense atrial cardiac signals and to provide right atrial chamber stimulation therapy, ICD 10 is coupled to implantable right atrial lead 20 having at least an atrial tip electrode 22, which typically is implanted in the patient's right atrial appendage.

To sense left atrial and ventricular cardiac signals and to provide left-chamber pacing therapy, ICD 10 is coupled to "coronary sinus" lead 24 designed for placement in the "coronary sinus region" via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

ICD 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, right ventricular lead 30 is transvenously inserted into heart 12 so as to place the right ventricular tip electrode 32 in the right ventricular apex so that RV coil electrode 36 will be positioned in the right ventricle and SVC coil electrode 38 will be positioned in the superior vena cava. Accordingly, right ventricular lead 30 is capable of receiving cardiac signals and delivering stimulation in the form of pacing and shock therapy to the right ventricle.

FIG. 1B shows a simplified block diagram of ICD 10, which is capable of treating both fast and slow arrhythmias with stimulation therapy, including cardioversion, defibrillation, and pacing stimulation. While a particular multi-chamber device is shown, it is shown for illustration purposes only, and one of skill in the art could readily duplicate, eliminate or disable the appropriate circuitry in any desired combination to provide a device capable of treating the appropriate chamber(s) with the desired cardioversion, defibrillation and pacing stimulation.

A housing 40 of ICD 10, shown schematically in FIG. 1B, is often referred to as the "can," "case" or "case electrode" and may be programmably selected to act as the return electrode for all "unipolar" modes. Housing 40 may further be used as a return electrode alone or in combination with one or more of coil electrodes, 28, 36, and 38 for shocking purposes. Housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal (AR TIP) 42 adapted for connection to atrial tip electrode 22.

To achieve left chamber sensing, pacing and shocking, the connector includes at least a left ventricular tip terminal (VL TIP) 44, a left atrial ring terminal (AL RING) 46, and a left atrial shocking terminal (AL COIL) 48, which are adapted for connection to left ventricular ring electrode 26, left atrial tip electrode 27, and left atrial coil electrode 28, respectively.

To support right chamber sensing, pacing, and shocking the connector also includes a right ventricular tip terminal (VR TIP) 52, a right ventricular ring terminal (VR RING) 54, a right ventricular shocking terminal (RV COIL) 56, and an SVC shocking terminal (SVC COIL) 58, which are configured for connection to right ventricular tip electrode 32, right ventricular ring electrode 34, RV coil electrode 36, and SVC coil electrode 38, respectively.

At the core of ICD 10 is a programmable microcontroller 60 which controls the various modes of stimulation therapy. As is well known in the art, microcontroller 60 typically includes a microprocessor, or equivalent control circuitry, designed specifically for controlling the delivery of stimulation therapy and can further include RAM or ROM memory, logic and timing circuitry, state machine circuitry, and I/O circuitry. Typically, microcontroller 60 includes the ability to process or monitor input signals (data) as controlled by a program code stored in a designated block of memory. The details of the design of microcontroller 60 are not critical to the present invention. Rather, any suitable microcontroller 60 can be used to carry out the functions described herein. The use of microprocessor-based control circuits for performing timing and data analysis functions are well known in the art. In specific embodiments of the present invention, microcontroller 60 performs some or all of the steps associated with the exercise diagnostics in accordance with the present invention.

Representative types of control circuitry that may be used with the invention include the microprocessor-based control system of U.S. Pat. No. 4,940,052 (Mann et al.) and the state-machines of U.S. Pat. Nos. 4,712,555 (Thornander et al.) and 4,944,298 (Sholder). For a more detailed description of the various timing intervals used within the ICDs and their inter-relationship, see U.S. Pat. No. 4,788,980 (Mann et al.). The '052, '555, '298 and '980 patents are incorporated herein by reference.

As shown in FIG. 1B, an atrial pulse generator 70 and a ventricular pulse generator 72 generate pacing stimulation pulses for delivery by right atrial lead 20, right ventricular lead 30, and/or coronary sinus lead 24 via an electrode configuration switch 74. It is understood that in order to provide stimulation therapy in each of the four chambers of the heart, atrial and ventricular pulse generators 70, 72, may include dedicated, independent pulse generators, multiplexed pulse generators, or shared pulse generators. Pulse generators 70 and 72 are controlled by microcontroller 60 via appropriate control signals 76 and 78, respectively, to trigger or inhibit the stimulation pulses.

Microcontroller 60 further includes timing control circuitry 79 which is used to control pacing parameters (e.g., the timing of stimulation pulses) as well as to keep track of the timing of refractory periods, PVARP intervals, noise detection windows, evoked response windows, alert intervals, marker channel timing, etc., which are well known in the art. Examples of pacing parameters include, but are not limited to, atrio-ventricular (AV) delay, interventricular (RV-LV) delay, atrial interconduction (A-A) delay, ventricular interconduction (V-V) delay, and pacing rate.

Switch 74 includes a plurality of switches for connecting the desired electrodes to the appropriate I/O circuits, thereby providing complete electrode programmability. Accordingly, switch 74, in response to a control signal 80 from microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to right atrial lead 20, coronary sinus lead 24, and right ventricular lead 30, through switch 74 for detecting the presence of cardiac activity in each of the four chambers of the heart. Accordingly, the atrial (ATR. SENSE) and ventricular (VTR. SENSE) sensing circuits 82 and 84 may include dedicated sense amplifiers, multiplexed amplifiers, or shared amplifiers. Switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic sensitivity control enables ICD 10 to deal effectively with the difficult problem of sensing the low amplitude signal characteristics of atrial or ventricular fibrillation. Such sensing circuits, 82 and 84, can be used to determine cardiac performance values used in the present invention.

The outputs of atrial and ventricular sensing circuits 82 and 84 are connected to microcontroller 60 which, in turn, are able to trigger or inhibit atrial and ventricular pulse generators, 70 and 72, respectively, in a demand fashion in response to the absence or presence of cardiac activity, in the appropriate chambers of the heart. Sensing circuits 82 and 84, in turn, receive control signals over signal lines 86 and 88 from microcontroller 60 for purposes of measuring cardiac performance at appropriate times, and for controlling the gain, threshold, polarization charge removal circuitry (not shown), and timing of any blocking circuitry (not shown) coupled to the inputs of sensing circuits 82 and 84.

For arrhythmia detection, ICD 10 utilizes the atrial and ventricular sensing circuits 82 and 84 to sense cardiac signals to determine whether a rhythm is physiologic or pathologic. The timing intervals between sensed events (e.g., P-waves, R-waves, and depolarization signals associated with fibrillation which are sometimes referred to as "F-waves" or "Fib-waves") are then classified by microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Microcontroller 60 utilizes arrhythmia detection circuitry 75 and morphology detection circuitry 76 to recognize and classify arrhythmia so that appropriate therapy can be delivered.

Cardiac signals are also applied to the inputs of an analog-to-digital (N/D) data acquisition system 90. Data acquisition system 90 is configured to acquire intracardiac electrogram signals, convert the raw analog data into a digital signal, and store the digital signals for later processing and/or telemetric transmission to an external device 102. Data acquisition system 90 is coupled to right atrial lead 20, coronary sinus lead 24, and right ventricular lead 30 through switch 74 to sample cardiac signals across any pair of desired electrodes.

Advantageously, data acquisition system 90 can be coupled to microcontroller 60, or other detection circuitry, for detecting an evoked response from heart 12 in response to an applied stimulus, thereby aiding in the detection of "capture." Capture occurs when an electrical stimulus applied to the heart is of sufficient energy to depolarize the cardiac tissue, thereby causing the heart muscle to contract. Microcontroller 60 detects a depolarization signal during a window following a stimulation pulse, the presence of which indicates that capture has occurred. Microcontroller 60 enables capture detection by triggering ventricular pulse generator 72 to generate a stimulation pulse, starting a capture detection window using timing control circuitry 79 within microcontroller 60, and enabling data acquisition system 90 via control signal 92 to sample the cardiac signal that falls in the capture detection window and, based on the amplitude, determines if capture has occurred.

The implementation of capture detection circuitry and algorithms are well known. See for example, U.S. Pat. No. 4,729,376 (DeCote, Jr.); U.S. Patent No. 4,708,142 (DeCote, Jr.); U.S. Pat. No. 4,686,988 (Sholder); U.S. Pat. No. 4,969,467 (Callaghan et al.); and U.S. Pat. No. 5,350,410 (Kleks et al.), which patents are hereby incorporated herein by reference. The type of capture detection system used is not critical to the present invention. Microcontroller 60 also contains maximum observed heart rate ($HR_{max}$) detector 62, workload detector 64, and/or a heart rate recovery detector 66. The operation of the $HR_{max}$ detector, workload detector, and heart rate recovery detector are discussed below in connection with the methods of the present invention.

Microcontroller 60 is further coupled to a memory 94 by a suitable data/address bus 96, wherein the programmable operating parameters used by microcontroller 60 are stored and modified, as required, in order to customize the operation of ICD 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of ICD 10 may be non-invasively programmed into memory 94 through a telemetry circuit 100 in telemetric communication with external device 102, such as a programmer, transtelephonic transceiver, or a diagnostic system analyzer. Telemetry circuit 100 is activated by microcontroller 60 by a control signal 106. Telemetry circuit 100 advantageously allows intracardiac electrograms and status information relating to the operation of ICD 10 (as contained in microcontroller 60 or memory 94) to be sent to external device 102 through an established communication link 104.

For examples of such devices, see U.S. Pat. No. 4,809,697, entitled "Interactive Programming and Diagnostic System for use with Implantable Pacemaker" (Causey, III et al.); U.S. Pat. No. 4,944,299, entitled "High Speed Digital Telemetry System for Implantable Device" (Silvian); and U.S. Pat. No. 6,275,734, entitled "Efficient Generation of Sensing Signals in an Implantable Medical Device such as a Pacemaker or ICD" (McClure et al.), which patents are hereby incorporated herein by reference.

In one embodiment, ICD 10 further includes a physiologic sensor 108 that can be used to detect changes in cardiac performance or changes in the physiological condition of the heart. Accordingly, microcontroller 60 can respond by adjusting the various pacing parameters (such as rate, AV Delay, RV-LV Delay, V-V Delay, etc.) in accordance with the embodiments of the present invention. Microcontroller 60 controls adjustments of pacing parameters by, for example, controlling the stimulation pulses generated by the atrial and ventricular pulse generators 70 and 72. While shown as being included within ICD 10, it is to be understood that physiologic sensor 108 may also be external to ICD 10, yet still be implanted within or carried by the patient. More specifically, sensor 108 can be located inside ICD 10, on the surface of ICD 10, in a header of ICD 10, or on a lead (which can be placed inside or outside the bloodstream). As discussed below, sensor 108 can also be used to measure activity level.

ICD 10 additionally includes a battery 110 which provides operating power to all of the circuits shown in FIG. 1B. For ICD 10, which employs shocking therapy, battery 110 must be capable of operating at low current drains for long periods of time, and then be capable of providing high-current pulses (for capacitor charging) when the patient requires a shock pulse. Battery 110 must also have a predictable discharge characteristic so that elective replacement time can be detected. Accordingly, ICD 10 preferably employs lithium/silver vanadium oxide batteries, as is true for most (if not all) current devices.

ICD 10 further includes a magnet detection circuitry (not shown), coupled to microcontroller 60. It is the purpose of the magnet detection circuitry to detect when a magnet is placed over ICD 10, which magnet may be used by a clinician to perform various test functions of ICD 10 and/or to signal microcontroller 60 that the external programmer 102 is in place to receive or transmit data to microcontroller 60 through telemetry circuit 100.

As further shown in FIG. 1B, ICD 10 is shown as having an impedance measuring circuit 112 which is enabled by microcontroller 60 via a control signal 114. The known uses for an impedance measuring circuit 120 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 112 is advantageously coupled to switch 74 so that any desired electrode may be used. The impedance measuring circuit 112 is not critical to the present invention and is shown only for completeness.

In the case where ICD 10 is intended to operate as a cardioverter, pacer or defibrillator, it must detect the occurrence of an arrhythmia and automatically apply an appropriate electrical therapy to the heart aimed at terminating the detected arrhythmia. To this end, microcontroller 60 further controls a shocking circuit 116 by way of a control signal 118. The shocking circuit 116 generates shocking pulses of low (up to 0.5 Joules), moderate (0.5-10 Joules), or high energy (11 to 40 Joules), as controlled by microcontroller 60. Such shocking pulses are applied to the patient's heart 12 through at least two shocking electrodes (e.g., selected from left atrial coil electrode 28, RV coil electrode 36, and SVC coil electrode 38). As noted above, housing 40 may act as an active electrode in combination with RV electrode 36, or as part of a split electrical vector using SVC coil electrode 38 or left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 Joules), delivered asynchronously (since R-waves may be too disorganized to be recognized), and pertaining exclusively to the treatment of fibrillation. Accordingly, microcontroller 60 is capable of controlling the synchronous or asynchronous delivery of the shocking pulses.

Figure 2:
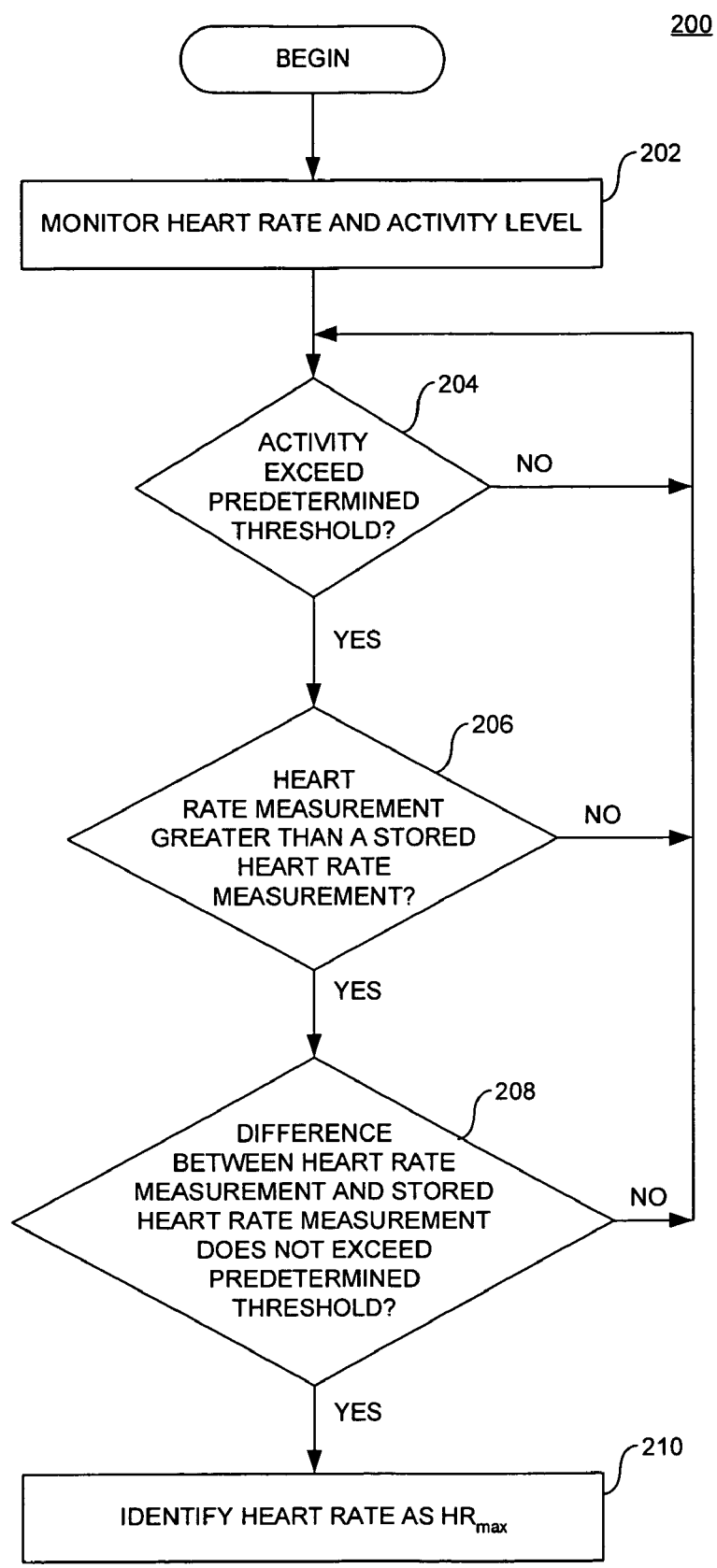
FIG. 2 is a flow chart illustrating an embodiment of a method for determining an observed maximum heart rate of a patient during exercise in accordance with the present invention.

With the description of an example environment, such as an ICD, in mind, features of the present invention are described in more detail below. A method 200 of determining a maximum observed heart rate ($HR_{max}$) of a patient during exercise in accordance with the present invention is illustrated in FIG. 2. According to an embodiment of the invention, the method 200 begins at step 202, in which the heart rate and activity level of the patient are monitored. The heart rate and activity level of the patient may be continuously monitored during the method 200.

The patient's heart rate may be determined by any suitable method. Many variations on how to determine heart rate are known to those of ordinary skill in the art, and any of these of reasonable accuracy may be used for the purposes of the invention. In embodiments of the invention, heart rate can be determined by measurement of an R-R interval cycle length (or P-P), which is the inverse of heart rate. As used herein, the heart rate (in beats per second) can be seen as the inverse to cycle length, determined by 60,000 divided by the cycle length (in milliseconds).

Heart rate measurements can be produced based upon the monitored heart rate. Such heart rate measurements include but are not limited to heart rate and heart rate intensity.

The activity level of the patient may also be determined by any suitable method. For example, the activity level may be determined by an accelerometer, piezoelectric crystal, minute ventilation, photoplethysmography, or a derivative thereof, such as the sensor indicated rate. In one embodiment, activity level is determined using physiologic sensor 108. In this embodiment, sensor 108 is an accelerometer, a piezoelectric crystal, an impedance sensor, or a photoplethysmography sensor.

In step 204, the measured activity level is compared with a predetermined activity threshold to determine whether the activity level exceeds the threshold. The predetermined activity threshold can be a value that corresponds to a certain level of exercise. It should be appreciated that the activity threshold value can be tailored for a specific patient's condition. Illustratively, an activity threshold value which correlates with walking or some other low level of exercise may be, for example, 50 milligravities as measured by an accelerometer.

It should be understood that in the context of the present invention, when comparing a measurement to a threshold, the terms "exceeds" or "is greater than" encompass instances when the measurement is equal to the threshold value. Similarly, it should be understood that the terms "falls below" or "is less than" a threshold value encompass instances when the measurement is equal to the threshold value. A person skilled in the relevant art will recognize that selection of a threshold value, and how to treat the condition of equality between the threshold and the measurement, are design choices.

The activity level can be compared with an activity threshold at various time intervals or periodically to determine whether the activity level exceeds the predetermined threshold. The particular selected time interval for monitoring is not critical. In one embodiment of the invention, the activity level is monitored and compared with the activity threshold at time intervals of 30 seconds (i.e., every 30 seconds).

If the patient activity level exceeds the predetermined activity threshold, then the method proceeds to step 206. Illustratively, if 50 milligravities activity is a threshold that correlates well with walking or some low level of exercise, and the implantable medical device is programmed at this threshold, then if the measured activity level exceeds 50 milligravities, the method proceeds to step 206.

Steps 206 and 208 can be performed when the patient activity level exceeds the predetermined activity threshold for a predetermined period of time. This predetermined period of time can be an amount that one skilled in the art would understand to be sufficient for the heart to react to the exercise by the patient (which can be indicated by, e.g., the activity level exceeding the predetermined activity threshold). Illustratively, the predetermined period of time may be 10 seconds to five minutes, preferably about two to three minutes, more preferably about two minutes.

In step 206, a heart rate measurement is compared with a stored heart rate measurement. The stored heart rate measurement can be, for example, a heart rate measurement previously obtained during exercise, including a previously determined $HR_{max}$ during exercise. Prior to first occurrence of the method, the stored heart rate measurement can be set to a predetermined default value. If the heart rate measurement exceeds the previously stored heart rate measurement, then the method proceeds to step 208. Otherwise, step 204 is repeated. That is, the method continues to monitor heart rate and activity level and produce heart rate measurements.

In step 208, the difference between the heart rate measurement and the stored heart rate measurement is compared to a predetermined threshold. The predetermined threshold difference may be selected to correspond to a value above which may be indicative of noise, PACs, PVCs, and/or arrhythmias. If the difference between the heart rate measurement and the stored heart rate measurement exceeds the threshold difference, the measured heart rate is not considered to be a $HR_{max}$. The threshold may even be step-size units, so as to show a gradual (physiologic) increase.

In accordance with one embodiment of the invention, step 208 is not performed. However, this embodiment is less preferred, as the resulting $HR_{max}$ could be inaccurate due to noise and/or premature heartbeats.

It should be understood that the order of comparison steps 206 and 208 is not limited to that depicted in the figure and may be performed in reverse order or conducted simultaneously.

If, in step 206, the heart rate measurement is greater than the stored heart rate measurement and, in step 208, the difference between the heart rate measurement and the stored heart rate measurement does not exceed a predetermined threshold, then the heart rate associated with the heart rate measurement may be identified as a maximum observed heart rate ($HR_{max}$). In other words, a heart rate can be identified as a $HR_{max}$ when the comparison steps 204, 206, and 208 are met.

The maximum observed heart rate may be recorded as a stored value, and the method 200 repeated, using the $HR_{max}$ as a new stored heart rate measurement. The $HR_{max}$ determination may be continued until activity level and/or heart rate is indicative of a slow-down of exercise.

Based on the $HR_{max}$ obtained, further values may be obtained that are indicative of heart conditioning. These values include heart rate intensity, percent oxygen consumption (% $VO_2$) reserve, metabolic equivalents (METS), percentage METS, workload, and absolute oxygen uptake.

For example, heart rate intensity (also known as percent heart rate reserve, heart rate capacity, target heart rate, or % HRR) may be calculated by dividing $HR_{max}$ by the predicted age compensated maximum heart rate as follows:

$$\%HRR = \frac{HR_{max} - \text{Resting } HR}{\text{Age compensated maximum } HR - \text{Resting } HR} * 100$$

In the equation indicated above, resting heart rate of the patient may be obtained by any suitable method including, for example, a heart rate measurement taken when the activity level of the patient is sufficiently low to be considered inactive. The age compensated maximum heart rate can be calculated by the formula: (220−age).

With % HRR, it is also possible to calculate % $VO_2$ reserve. Swain et al. have shown a close correlation between % HRR and % $VO_2$ reserve ("Heart rate reserve is equivalent to % $VO_2$ reserve, not % $VO_{2max}$," Med Sci. Sports Exercise 29:410-414 (1997)).

% $VO_2$ reserve is an intensity scale or index that describes the percentage of oxygen intake used during exercise. The value between % $VO_2$ reserve and 100% is the amount of oxygen intake reserves available. This value may be obtained by the following equation (Swain et al., Target HR for the development of CV fitness, Medicine & Science in Sports & Exercise 26(1):112-116):

% $VO_2$ reserve=(% HRR−37)/0.64 where % HRR is calculated as described above.

Workload is measure of intensity times duration, and may be seen by the following equation:

Workload=Intensity*Duration where Intensity is $VO_{2observed}$, but may also be seen as an index such as heart rate intensity (% HRR) or % $VO_2$ reserve as discussed above, and Duration is the time during exercise when activity is above a predetermined threshold. It is possible to use in the calculation of work only % HRR values above a predetermined threshold (e.g., >40%), reflective of at least moderate exercise. An additional method involves multiplying the mean % HRR above the predetermined threshold by the total duration.

A primary expression of intensity throughout the clinical community is metabolic equivalents (METS). METS is a measure of Intensity or functional capacity. One (1) MET is equivalent to the amount of energy used at rest (oxygen uptake of 3.5 ml/(kg*min)), or the resting $VO_2$.

1 MET=3.5 mL/(kg*min)=$VO_{2\ resting}$

METS are linked to heart rate intensity. See, Strath et al., "Evaluation of Heart Rate as a Method for Accessing Moderate Intensity Physical Activity," Med. & Sci. in Sports & Exerc., 465-470 (2000).

One method for determining METS has been described by Wilkoff, B. L., et al. ("A Mathematical Model of the Cardiac Chronotropic Response to Exercise," J. Electrophysiol. 3:176-180 (1989)), in which a mathematical model was developed describing the relationship of percentage metabolic equivalents (% METS) to heart rate intensity using the CAEP and Bruce exercise protocols. They found that the relationship was linear, with a slope of approximately 1 (1.06), by the equation:

% METS=1.06*(% HRR)−4.87

Observed METS during exercise can be obtained through the following equation:

$$\%\text{METS} = \frac{(\text{METS}_{observed} - \text{METS}_{rest})}{(\text{METS}_{max} - \text{METS}_{rest})} * 100\% \text{ with METS}_{rest} = 1$$

The value for $METS_{max}$ to be used in the above equation may be obtained as follows:

Predicted $METS_{max}$=16.6−0.16(age)

This predicted $METS_{max}$ value is an approximation, as it was obtained by a nomogram of sedentary men who participated in the USAir Force School of Aerospace Medicine Protocol, and who did not have a history of CHF. See Morris et al., "Nomogram Based on Metabolic Equivalents and Age for Assessing Aerobic Exercise Capacity in Men," J. Am. Coll. Cardiol. 22:175-182 (1993). However, if this approximation is used as a best fit method for maximal METS expected for each patient, $METS_{observed}$ can thus be calculated as:

$METS_{observed}$=(% METS/100)*((16.6−0.16*(age))−1)+1

METS can also be determined by the following method by alternatively solving for % $VO_2$ reserve. % $VO_2$ reserve can be calculated by the following equation:

$$\%VO_2\text{reserve} = \frac{(VO_{2observed} - VO_{2rest})}{(VO_{2max} - VO_{2rest})} * 100\% \text{ with } VO_{2rest} = 1$$

where $VO_{2max}$ can be obtained from the non-exercise prediction equation of Jackson et al., "Prediction of functional aerobic capacity without exercise testing," Med. Sci. Sports & Exerc J. 22:863-870 (1990) by:

$VO_{2max}$=50.513+1.589*(activity scale[0 . . . 7])−0.289*(age)−0.552*(% fat)+5.863*(F=0,M=1).

Or, for those times when % fat may be difficult to obtain, the following equation by Jackson et al. allows for use of Body Mass Index (BMI):

$VO_{2max}$=56.363+1.921*(activity scale[0 . . . 7])−0.381*(age)−0.754*(BMI)+10.987*(F=0,M=1)

In the above two equations for $VO_{2max}$, activity scale can be related to % HRR as a level of activity, % fat or BMI is either calculated as an average over the population or a value to be uploaded to the ICD, and F and M designate female and male, respectively.

When $VO_{2max}$ is plugged back into the % $VO_2$ equation, $VO_{2observed}$ can be obtained (units of mL/[kg*min]). $METS_{observed}$ can be obtained by dividing $VO_{2observed}$ by 3.5.

Another way to determine $VO_{2max}$ is by the Astrand single-stage submaximal method, with the following equation:

$VO_{2max}$=$VO_{2observed}$*[(Age compensated max. HR−K)/($HR_{observed}$−K)]

where K=63 for men and 73 for women. (Astrand, P. O., and Rodah, K., Textbook of Work Physiology, 3$^{rd}$ Ed. New York: McGraw-Hill, 1986, p. 318-325 and 340-358.)

Once $METS_{observed}$ has been calculated, it is possible to get the following values:

Relative Oxygen consumption (ml/(kg*min)): METS/3.5
Absolute Oxygen Uptake (L/min): $VO_{2max}$*Weight
Calories (kcal): 1 L $O_2$=5 kcal: ($VO_{2max}$*duration)/5
Joules: 1 Kcal=4186 J If the value for METS has a large standard deviation over the above equations, it can be further worked into a descriptive intensity scale (light, moderate, vigorous) as defined by Ainsworth BE et al., Compendium of physical activities: an update of activity codes and MET intensities, *Med Sci. Sports Exerc.*; 9:S498-S516 (2000)) where these can be defined by:

$$METS_{60\% \, max \, cardiorespiratory \, capacity} = [0.6*(60-0.55*(age)]/3.5 \text{ for men, and}$$

$$METS_{60\% \, max \, cardiorespiratory \, capacity} = [0.6*(48-0.37*(age)]/3.5 \text{ for women}$$

with 60% max cardiorespiratory capacity (MCC) considered vigorous. Therefore, light intensity would be, for example, between 20-40%, and moderate activity would be, for example, between 40-60%.

Figure 3A:
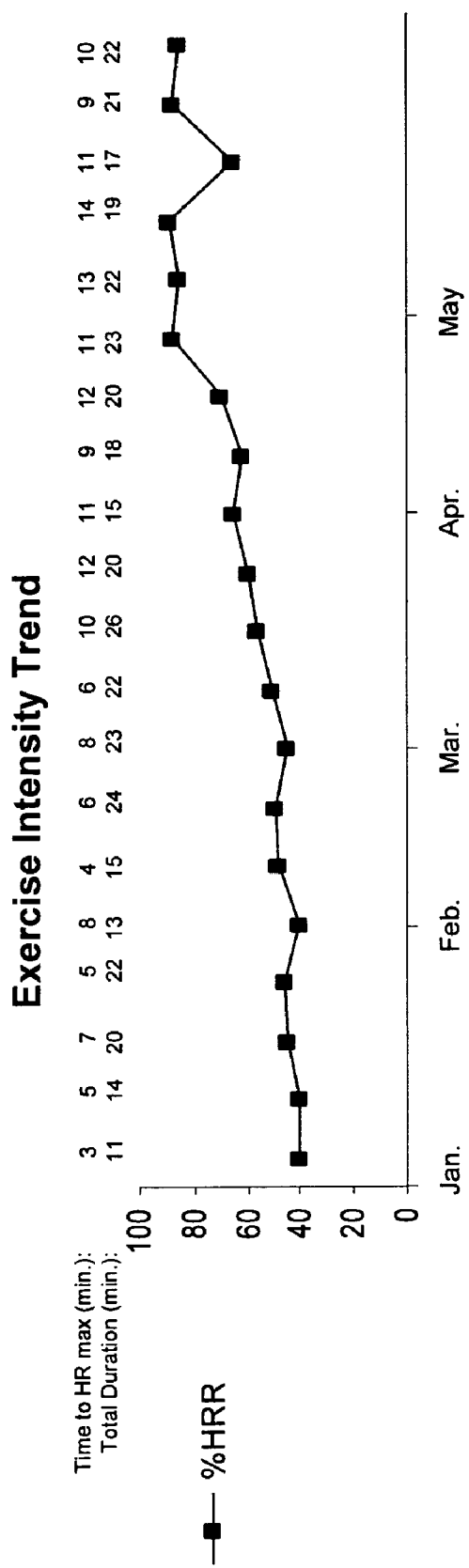
Figure 3B:
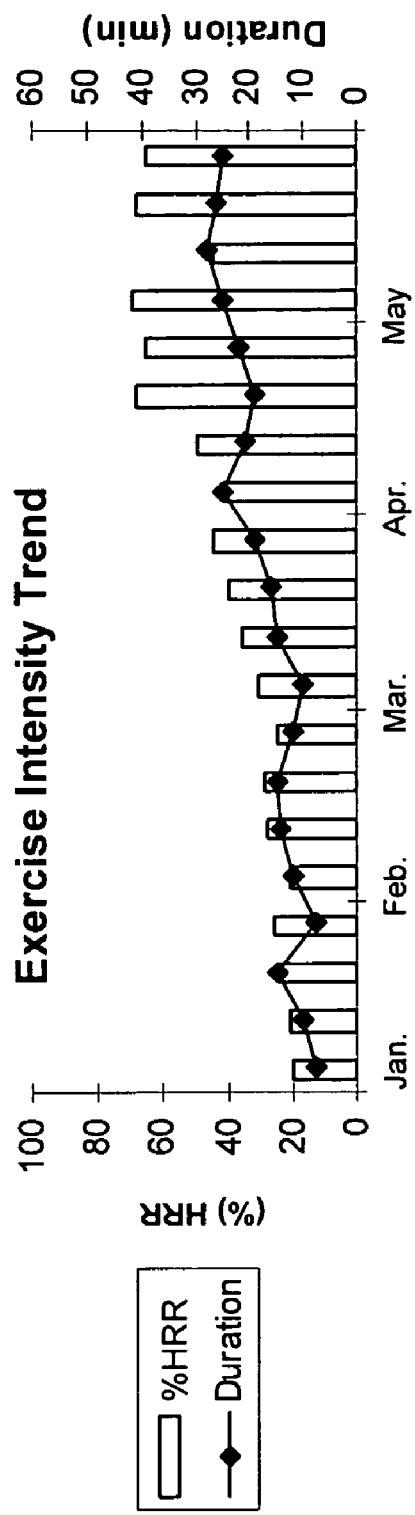
Figure 3C:
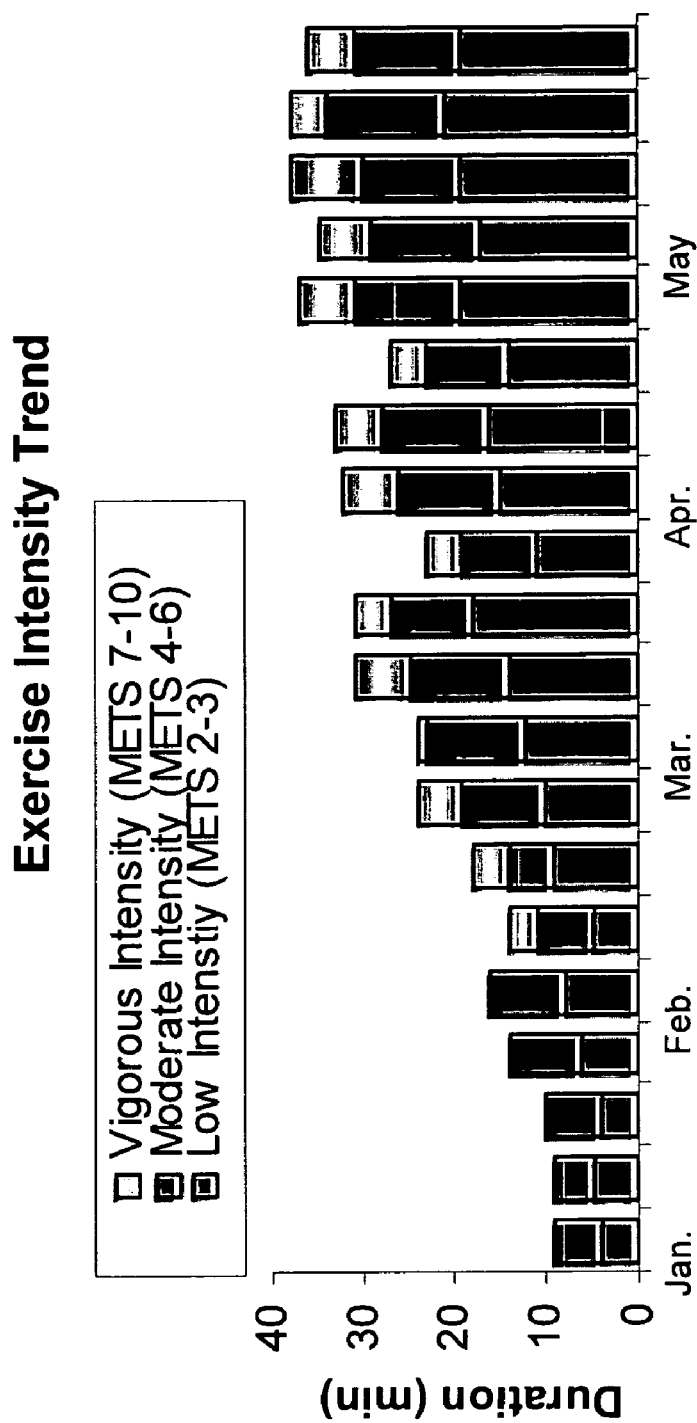
Figure 3D:
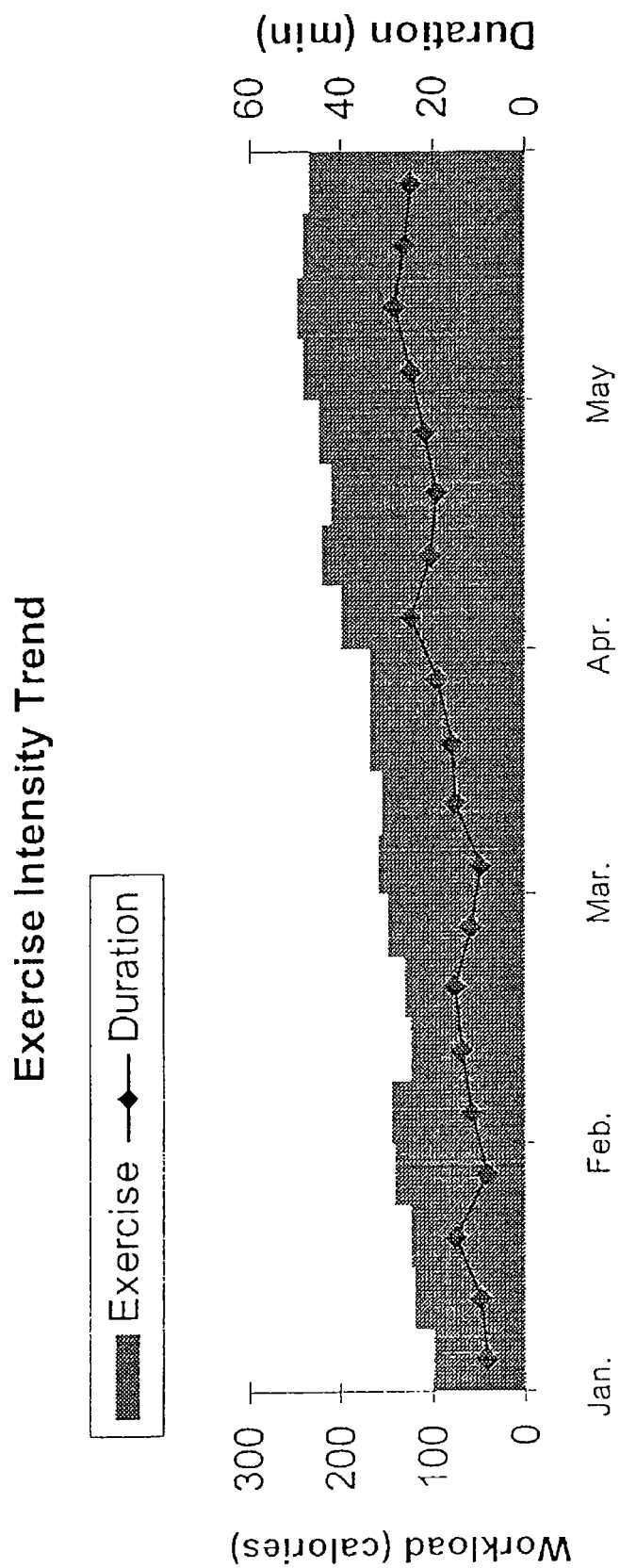

FIGS. 3A to 3D illustrate how exercise data, such as exercise intensities may be displayed. The data illustrated in these Figures are prophetic. In FIG. 3A, measured heart rate intensity (% HRR) data is displayed as a function of time in the graph. The table above the chart illustrates the corresponding time to $HR_{max}$ and the total duration of $HR_{max}$. In FIG. 3B, measured heart rate intensity and total duration of $HR_{max}$ are illustrated on one graph. In FIG. 3C, measured exercise intensity in the units of METS is illustrated, with corresponding amounts of vigorous, moderate, and low intensities, and the duration of each amount. In FIG. 3D, measured workload is illustrated, with corresponding duration of the workload. Each data point illustrated on the table and graphs of FIGS. 3A-3D represent an average over one week.

As is illustrated from FIGS. 3A-3D, the invention also encompasses determining the time period associated with exercise intensities. For example, the time to and duration of $HR_{max}$ and workload can be determined.

The above-described method 200 for determining the maximum observed heart rate of a patient during exercise may be implemented by hardware, software, or firmware of a pacing system, such as the ICD described earlier with reference to FIGS. 1A and 1B, with particular reference to $HR_{max}$ detector 62.

In another embodiment of the invention, a method for determining exercise diagnostics, such as workload, heart rate intensity, percent oxygen consumption (% $VO_2$) reserve, metabolic equivalents (METS), percentage METS, and absolute oxygen uptake may be obtained without obtaining $HR_{max}$. This method includes monitoring a changing heart rate of a patient and producing heart measurements, monitoring activity level, and determining an exercise diagnostic, such as workload of the patient using at least one heart rate measurement when the activity level exceeds an activity threshold.

A method 400 of determining workload of a patient during exercise in accordance with the present invention is illustrated in FIG. 4. According to an embodiment of the invention, the method 400 begins at step 402, in which the heart rate and activity level of the patient is monitored. The heart rate and activity level of the patient may be continuously monitored during the method 400.

As discussed above in conjunction with the method for determining $HR_{max}$, the patient's heart rate and activity level may be determined by any suitable method, and heart rate measurements can be generated based upon the monitored heart rate. In embodiments of the invention, the heart rate measurements include heart rate intensity.

In step 404, the measured activity level is compared with a predetermined activity threshold to determine whether the activity level exceeds the threshold. As discussed above, the predetermined activity threshold can be a value that corresponds to a certain level of exercise and can be tailored for a specific patient's condition.

The activity level can be compared with an activity threshold at various time intervals to determine whether the activity level exceeds the predetermined threshold for a predetermined period of time. The time interval or frequency of comparing the activity level with the activity threshold is not critical to the invention. In an embodiment of the invention, the activity level is monitored and compared with the activity threshold at time intervals of 30 seconds. If it is determined in step 404 that the patient activity level exceeds a predetermined activity threshold, then step 406 is performed. As discussed above in conjunction with determining $HR_{max}$, step 406 can be performed when the patient activity level exceeds the predetermined activity threshold for at least a predetermined period of time. This predetermined period of time may correlate to the amount of time for the heart to react to the exercise by the patient. Illustratively, the predetermined period of time may be 10 seconds to five minutes, preferably about two to three minutes, more preferably about two minutes.

In step 406, workload of the patient is determined using at least one heart rate measurement. Preferably, a heart rate measurement that is used to determine work of the patient during the exercise is heart rate intensity.

Specifically, workload of a patient during exercise can be determined by the summation of intensities over time over the full time of exercise (i.e., for the entire period that the activity level exceeds the predetermined threshold), where intensities are calculated from the previous equations discussed to obtain $VO_{2observed}$. Alternately, as discussed above, workload may be described as a unitless index by multiplying intensities such as % HRR or % $VO_2$ reserve and time. Illustratively, after the activity level exceeds an activity threshold, work values can be calculated (Intensity*Duration) for each datapoint until the cessation of exercise (i.e., when the activity level no longer exceeds the predetermined threshold)). The determination of work of the patient during the exercise can also be represented by the following formula:

$$\Sigma Intensity(x)*(Time(x)-Time(x-1))$$

where x=0:n.

Based on the workload value obtained above, other exercise diagnostics, such as heart rate intensity, percent oxygen consumption (% $VO_2$) reserve, metabolic equivalents (METS), percentage METS, and absolute oxygen uptake may be obtained. For example, heart rate intensity may be found by dividing the work by the total time of exercise.

The above-described method 400 for determining workload of a patient during exercise may be implemented by hardware, software, or firmware of a pacing system, such as the ICD described earlier with reference to FIGS. 1A and 1B, with particular reference to work detector 64.

The present invention is also directed to a method and device for determining heart rate recovery of a patient. Heart rate recovery involves analyzing how the heart recovers from a maximum rate during exercise. The heart rate recovery value may not change in a matter of days, but possibly in a matter of weeks. Obtaining the heart rate recovery value only during episodes of peak exercise, as opposed to any low-level exercise, may provide a more accurate reflection of cardiac health through heart rate recovery.

A method 500 of determining a measure of heart rate recovery in accordance with the present invention is illustrated in FIG. 5. According to an embodiment of the invention, the method 500 begins at step 502, in which the heart rate and activity level of the patient are monitored. The heart rate and activity level of the patient may be continuously monitored during the method 500. The heart rate and activity level can be monitored by any suitable method, including those discussed above.

Heart rate measurements can be produced based upon the monitored heart rate. As discussed above, such heart rate measurements include but are not limited to heart rate and heart rate intensity.

In step 504, a heart rate measurement is compared with a first heart rate measurement threshold, and an activity level is compared with a first activity threshold. The first heart rate measurement threshold and first activity threshold may be indicative of exercise, preferably vigorous or peak exercise.

In step 504, if a heart rate measurement exceeds a first heart rate measurement threshold, and/or an activity level exceeds a first activity threshold, then the method proceeds to step 506. In step 506, the heart rate is identified as a first heart rate. That is, the heart rate taken at the time (1) a heart rate measurement exceeded a first heart rate measurement threshold and/or (2) the activity level exceeded the first activity threshold is used as a first heart rate value for further computations.

In one embodiment of the invention, in step 504, the first heart rate is identified when at least one heart rate measurement exceeds the first heart rate measurement threshold. In another embodiment, the first heart rate is identified when at least one heart rate measurement exceeds the first heart rate measurement threshold for a predetermined period of time. In other embodiments, the first heart rate can be identified when an average value of heart measurements (taken over a predetermined time period, such as, for example, one minute) exceeds the first heart rate measurement threshold.

In another embodiment of the invention, the first heart rate can be identified when the activity level exceeds the first activity threshold. In yet another embodiment, the first heart rate can be identified when the activity level exceeds the first activity threshold for a predetermined period of time. In still yet another embodiment, the first heart rate can be identified when, for the predetermined period of time, an average activity level exceeds the first activity threshold.

Preferably, the first heart rate is identified when both the activity level exceeds a first activity threshold and a heart rate measurement exceeds a first heart rate measurement threshold.

Even more preferably, the first heart rate is identified when the mean activity level value exceeds a first activity threshold for a predetermined period of time, and a mean heart rate measurement value, such as heart rate intensity, exceeds a first heart rate measurement threshold for a predetermined period of time.

In accordance with embodiments of the invention, the first heart rate is identified only during peak exercise, only after a stringent set of conditions have been met. These conditions can include certain levels of heart rate intensity, activity level and duration of time. This first heart rate may be referred to as a peak exercise heart rate.

Illustratively, a peak exercise heart rate can be identified when the mean activity level exceeds a first activity threshold and the heart rate intensity exceeds a heart rate intensity threshold, such as, e.g., 80%, for a period of time of at least about five minutes.

As illustrated by step 508, heart rate and activity level continue to be monitored. It should be understood that the identified first heart rate can be overwritten by a subsequent heart rate (including a slower heart rate), provided that the first heart rate criteria described above are still met.

Heart rate and activity level also continue to be monitored, as illustrated by step 508, for determining the next parameter used to determine heart rate recovery, a second heart rate. The second heart rate is the heart rate after a slow-down in exercise, and is compared with the first heart rate to determine a measure of heart rate recovery. In accordance with embodiments of the present invention, heart rate measurements (such as, for example heart rate) continued to be produced.

In step 510, a heart rate measurement is compared with a second heart rate measurement threshold, and an activity level is compared with a second activity threshold. The second heart rate measurement threshold and second activity threshold can be indicative of a slowing down or cessation of exercise.

If a heart rate measurement falls below a second heart rate measurement threshold, and/or an activity level falls below a second activity threshold, then in step 512 the monitored heart rate is identified as a second heart rate.

In one embodiment of the invention, the second heart rate is identified when the activity level falls below the second activity threshold for a predetermined period of time. Preferably, the second heart rate is identified when a mean activity level falls below the second activity threshold for a predetermined period of time. The comparison can also be done based on an average activity level over a predetermined period of time.

In another embodiment of the invention, the second heart rate is identified when a heart rate measurement falls below a second heart rate measurement threshold for a predetermined period of time. For example, if a heart rate measurement (e.g. heart rate) falls below a predetermined threshold and/or the mean activity level falls below a predetermined activity threshold, then the heart rate and activity levels can be recorded for a predetermined period of time, such as, for example one, two, or three minutes.

After the predetermined period of time, if a heart rate measurement is less than the heart rate measurement prior to the predetermined period of time, and the activity level is less than a third activity threshold (which can be the same as or lower than the second activity threshold), then a second heart rate is identified. Preferably, the slowest heart rate measured during the predetermined period of time is identified as the second heart rate.

In step 514, once a first heart rate and a second heart rate are identified, the first and second heart rates are used to determine a measure of heart rate recovery. For example, the second heart rate is subtracted from the first heart rate to obtain a heart rate difference. The difference is a heart rate recovery value.

It should be understood that additional second heart rate values can be identified after the first heart rate and compared to the first heart rate to determine a measure of heart rate recovery. Accordingly, the term "second heart rate" is intended to encompass one or more heart rates that meet the above-described criteria for identification of the second heart rate. In other words, the second heart rate may be several heart rates over consecutive periods of time (e.g. minutes).

Illustratively, heart rates measured at discrete times after the identified first heart rate and that meet the second heart rate identification criteria can be compared with the first heart rate to determine a measure of heart rate recovery. For example, the difference between the first heart rate and each of the second heart rates can provide a measure of heart rate recovery. Also, a listing of the first heart rate and heart rates meeting the second heart rate criteria as they decrease over time can also be a measure of heart rate recovery.

The invention also encompasses identifying the first heart rate at the time the criteria for identifying the second heart rate is met. For example, if a heart rate measurement exceeds a first heart rate measurement threshold or an activity level exceeds a first activity threshold, and subsequently a heart rate measurement falls below a second heart rate measurement or the activity level falls below a second activity threshold, a first heart rate can be identified at or near the inflection point between meeting the first and second heart rate identification criteria.

The second heart rate then can be identified as one or more heart rates measured subsequent to the identified first heart rate. For example, provided that the measured heart rates meet the second heart rate identification criteria, a second heart rate can be identified one minute, two minutes, and/or three minutes following the first heart rate. The difference between the first heart rate and the second heart rate at one, two, and/or three minutes post-first heart rate identification provides values that determine a measure of heart rate recovery.

To illustrate, a patient exercises (e.g. runs) for five minutes, and then stops running and sits down for three minutes. Provided that the patient met the first and second heart rate identification criteria described above, the first heart rate would be identified at the five minute mark, and the second heart rates would be identified at the six, seven, and eight minute mark. The first heart rate would be compared with each of the second heart rates at the six, seven, and eight minute mark to determine a measure of heart rate recovery.

Preferably, in the method 500 for determining a measure of heart rate recovery, heart rate measurements are filtered to remove noise and premature heart beats such as arrhythmias, PACs, and PVCs.

The above-described method 500 for determining the measure of heart rate recovery of a patient may be implemented in software, or firmware of a pacing system, such as the ICD described earlier with reference to FIGS. 1A and 1B, with particular reference to HR Recovery Detector 66.

EXAMPLES

Example 1

Determination of Maximum Observed Heart Rate

A method for determining a maximum observed heart rate ($HR_{max}$) of a patient during exercise is illustrated in FIG. 6. To calculate $HR_{max}$ for exercise conditioning, it is preferred that the patient has maintained a certain level of activity for a certain period of time. Thus, in the illustrative method, the maximum observed heart rate is not calculated unless the activity level is above a threshold activity for a certain period of time.

In method 600, the current cycle length (inverse of heart rate) and activity level are obtained as illustrated in step 602. It should be understood that the cycle length and activity level can be continuously or periodically monitored.

In step 604, the activity level measured is compared with an activity threshold. If the activity is less than an activity threshold, then the method returns to step 602. In this manner, steps 602 and 604 result in a continuous (or, optionally, periodic) monitoring of activity level.

If the measured activity level is greater than the activity threshold, then in step 606 the elapsed time (i.e., the period during which the activity level is greater than the activity threshold) is compared with a time threshold. The time threshold can be, for example, 2-3 minutes. Once this comparison indicates that sufficient time has elapsed, then step 608 is performed. Thus, before step 608 is performed, there has been a sufficient activity level for a sufficient period of time to indicate actual exercise by the patient.

In step 608, the current cycle length is compared with the previous cycle lengths, preferably a previous average cycle length. In step 610, if the difference of cycle length is too large (e.g., greater than or equal to about 100 milliseconds), this may indicate noise, PACs, PVCs or arrhythmias, and will not be identified as the $HR_{max}$. If this occurs, as illustrated in step 610, the method returns to step 602 to obtain a new, current cycle length and activity.

In step 610, if the difference of cycle length is less than a threshold (indicating that the current cycle length is not due to noise or a premature heart beat), then in step 612, the current cycle length is compared with the previous cycle length. If the current recorded cycle length is not less than the previously recorded value, then the current cycle length is not identified as the $HR_{max}$, and step 602 is repeated. However, if the current cycle length is less than the previous recorded value, then in step 614 the current cycle length is identified and stored as the new $HR_{max}$.

Example 2

Method of Determining Heart Rate Recovery

A method for determining heart rate recovery of a patient is illustrated in FIG. 7.

In accordance with the illustrated method 700, the first heart rate, a peak exercise heart rate is obtained by analyzing cycle lengths only when the qualifications for $HR_{max}$ have been met.

In step 702, the current cycle length is obtained. In step 704, if the cycle length is near $HR_{max}$, the value of the heart rate intensity is determined. If this value is greater than a predetermined threshold such as, e.g., 65%, and if the length of time is greater than a predetermined threshold, such as, e.g., 5 minutes, then in step 706 the cycle length is recorded as the first, peak exercise heart rate. Otherwise, the heart rate intensity for each cycle length continues to be determined.

The cycle length recorded in step 706 is continuously or periodically recorded, and may be overwritten by slower rates. However, if a noticeable slowdown occurs, in step 708 a new buffer collects the recorded cycle length. In step 710, if the current cycle length is greater than a predetermined threshold, such as, e.g., 20 milliseconds, or the mean activity level is less than a predetermined threshold, each indicative of a drop in activity, then in step 712 cycle length values are continuously recorded for three minutes.

In step 714, if after three minutes, the cycle length is greater than the cycle length measured three minutes previously, and the activity level is less than a threshold value, then in step 716 the largest cycle length for each of the three minutes is recorded as the second set of heart rate recovery values. If these criteria in step 714 are not met, then in step 718 a second heart rate is not recorded, as the exercise is coming too slowly to a stop.

Once the cessation of exercise has been determined, in step 716 both the first, peak exercise heart rate and the three heart rate recovery value cycle lengths are converted to beats per minute and subtracted from each other. The values obtained are the times of heart rate recovery.

It will be appreciated by those skilled in the art that the above methods 200, 400, 500, 600, and 700 can be used within the hardware, software, and/or firmware of a pacing system, such as the ICD described earlier with reference to FIGS. 1A and 1B, for example.

Example embodiments of the methods, systems, and components of the present invention have been described herein. As noted elsewhere, these example embodiments have been described for illustrative purposes only, and are not limiting. Other embodiments are possible within the scope of the invention. Such embodiments will be apparent to persons skilled in the relevant art(s) based on the teachings contained herein.

For example, although the inventive methods are described with reference to an ICD, the methods are not limited to such a use. Illustratively, the inventive methods could be carried out with one or more external devices affixed to a patient's body to monitor heart rate and activity level, produce heart rate measurements and to determine exercise diagnostics such as, for example $HR_{max}$, work, and heart rate recovery. Illustratively, the patient may have affixed to their body a hotter recording device to measure heart rate and an accelerometer to determine activity level.

Thus, the breadth and scope of the present invention should not be limited by any of the above-described exemplary embodiments, but should be defined only in accordance with the following claims and their equivalents.

What is claimed is:

1. In an implantable cardiac device, a method for determining workload of a patient during exercise, comprising:
   (a) monitoring a changing heart rate of the patient and producing heart rate measurements;
   (b) monitoring activity level of the patient; and
   (c) determining workload of the patient using at least one heart rate measurement when the activity level exceeds an activity threshold.

2. The method of claim 1, wherein step (c) comprises determining workload of the patient when the activity level exceeds the activity threshold for a predetermined period of time.

3. The method of claim 1, wherein step (c) comprises determining workload of the patient using heart rate measurements over a predetermined period of time.

4. The method of claim 1, further comprising determining one or more of the following: heart rate intensity, percent oxygen consumption (% $VO_2$) reserve, metabolic equivalents (METS), and percentage METS.

5. An implantable cardiac device for determining workload of a patient during exercise, comprising:
   means for monitoring a changing heart rate of the patient and producing heart rate measurements;
   means for monitoring activity level of the patient;
   means for determining work of the patient using at least one heart rate measurement when the activity level exceeds an activity threshold; and
   means for transmitting the work of the patient to an external device.

6. A computer readable medium having instructions that when executed on a processor of an implantable medical device (IMD) have cardiac pacing capabilities cause the IMD to:
   (a) monitor a changing heart rate of the patient and produce heart rate measurements;
   (b) monitor activity level of the patient; and
   (c) determine workload of the patient using at least one heart rate measurement when the activity level exceeds an activity threshold, wherein workload is calculated as the product of heart rate intensity and duration, wherein duration is the period of time during which the activity level exceeds an activity threshold.

7. The computer readable medium of claim 6, wherein the instructions cause the processor to determine workload of the patient using at least one heart rate measurement when the activity level exceeds an activity threshold for at least a predetermined period of time.

8. The computer readable medium of claim 6, wherein intensity is $VO_{2observed}$.

9. The computer readable medium of claim 6, wherein intensity is % $VO_2$ reserve.

10. The computer readable medium of claim 6, wherein the instructions further cause the processor to:
   (d) identify a heart rate as the maximum observed heart rate using the IMD; and
   (e) store the identified maximum observed heart rate in the IMD, when the following conditions occur: (i) the activity level exceeds an activity threshold for a predetermined period of time, (ii) a heart rate measurement is greater than a stored heart rate measurement, and (iii) a difference between the heart rate measurement and the stored heart rate measurement does not exceed a predetermined threshold; and
   (f) determine heart rate intensity using the formula:

$$\%HRR = \frac{HR_{max} - \text{Resting } HR}{\text{Age compensated maximum } HR - \text{Resting } HR} * 100.$$

11. The computer readable medium of claim 10, wherein the instruction further cause the processor to determine a metabolic equivalents (METS).

12. The computer readable medium of claim 10, wherein the instruction further cause the processor to determine a percentage metabolic equivalents (METS).

13. The computer readable medium of claim 6, wherein the instructions cause the processor to determine workload of the patient using at least one heart rate measurement when the activity level exceeds an activity threshold and the heart rate intensity exceeds an intensity threshold.

14. The computer readable medium of claim 6, wherein the instruction further cause the processor to determine a percentage metabolic equivalents (METS).

* * * * *

UNITED STATES PATENT AND TRADEMARK OFFICE
CERTIFICATE OF CORRECTION

PATENT NO.         : 7,668,590 B1                                    Page 1 of 1
APPLICATION NO. : 11/351401
DATED              : February 23, 2010
INVENTOR(S)        : Michael Paris It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 996 days.

Signed and Sealed this

Seventh Day of December, 2010

David J. Kappos
*Director of the United States Patent and Trademark Office*